United States Patent [19]

Yanagihara et al.

[11] Patent Number: 4,693,799

[45] Date of Patent: Sep. 15, 1987

[54] PROCESS FOR PRODUCING PLASMA POLYMERIZED FILM

[75] Inventors: Kenji Yanagihara; Mituo Kimura, both of Yokohama; Masahiro Niinomi, Machida; Yasuo Nishikawa, Odawara; Yoshito Mukaida, Kanagawa, all of Japan

[73] Assignees: Japan Synthetic Rubber Co., Ltd., Tokyo; Fuji Photo Film Co., Ltd., Minamiashigara, both of Japan

[21] Appl. No.: 841,183

[22] Filed: Mar. 19, 1986

[30] Foreign Application Priority Data

Mar. 19, 1985 [JP] Japan ................................ 60-055549

[51] Int. Cl.$^4$ ........................ C07C 3/24; C23B 13/00

[52] U.S. Cl. .................................. 204/165; 204/168; 204/169; 427/424

[58] Field of Search ...................... 204/165, 168, 169; 427/424

[56] References Cited

U.S. PATENT DOCUMENTS 3,471,316 10/1969 Manuel ................................ 204/165

OTHER PUBLICATIONS

Tkachuk et al., Polymer Science, USSR, vol. 16, No. 7, (1974), pp. 1860–1869.

*Primary Examiner*—Arthur P. Demers

*Attorney, Agent, or Firm*—Oblon, Fisher, Spivak, McClelland, & Maier

[57] ABSTRACT

A process for producing a plasma polymerized film, which comprises forming a plasma polymerized film on the surface of a substrate placed in a reaction zone by subjecting an organic compound containing gas to plasma polymerization utilizing low temperature plasma formed by pulse discharging, in which the time for non-discharge condition is at least 1 msec. and the voltage rise time for gas breakdown is not longer than 100 msec. The plasma polymerized film obtained has a small coefficient of friction, high lubricity, durability and heat resistance and is useful as a solid lubricating film, etc.

14 Claims, 4 Drawing Figures

PROCESS FOR PRODUCING PLASMA POLYMERIZED FILM

BACKGROUND OF THE INVENTION

1. Field of the Invention

This invention relates to a process for producing a plasma polymerized film by utilizing low temperature plasma, particularly to a process for producing a plasma polymerized film by pulse discharging.

2. Description of the Prior Art

In use, magnetic tapes, magnetic discs, and the like are placed in a sliding relationship with structural elements, mechanical members, and the like, and the surfaces in sliding contact require lubricity with a small coefficient of friction.

One of the methods known in the art for improving the lubricity of such a sliding surface is to coat the sliding surface with an organic lubricant comprising a fatty acid, and it has been utilized for magnetic tapes, magnetic discs, etc. However, this method has drawbacks in that the lubricant cannot easily be applied uniformly on the sliding surface, the effect may differ depending on the material of the surface to be coated and therefore no satisfactory lubricity can necessarily be obtained, the durability of lubricity is poor because the lubricant is lost gradually by repeated use, and that it has no heat resistance and therefore cannot be used at high temperatures. In addition, it is not applicable for precision machines such as watches and robots. Another method for improvement of lubricity is the method in which the sliding surface is coated with inorganic powder such as graphite powder, molybdenum sulfide powder, lead oxide, calcium fluoride, etc. This method has been utilized for mechanical elements such as gears, bearings, etc. However, this method also involves the same drawbacks as the above organic lubricant. Still another method known in the art is to form a solid lubricating film composed of, for example, polytetrafluoroethylene on the sliding surface and it has been used for sliding surfaces for which chemical resistance is required and sliding surfaces for which heat resistance is required. However, since the lubricating film which can be formed is considerably thick on the order of several tens microns or more, it has the drawback of being not applicable for the bearings, gears, and other such parts of precision machines, video heads, magnetic tapes, magnetic discs and others.

SUMMARY OF THE INVENTION

Accordingly, an object of the present invention is to provide a process for producing a plasma polymerized film having low coefficient of friction, excellent lubricity even with a very thin film, and good durability and heat resistance.

The present invention provides a process for producing a plasma polymerized film, which comprises forming a plasma polymerized film on the surface of a substrate placed in a reaction zone by subjecting an organic compound containing gas to plasma polymerization utilizing low temperature plasma formed by pulse discharging, in which the time of non-discharge condition is at least 1 msec. and the voltage rise time for gas breakdown is not longer than 100 msec.

Low temperature plasma, which as used herein is a term used in contrast to high temperature plasma, means a plasma in which the electron temperature is tens of thousands K. but neutral gas temperature and ion temperature are 2,000 K. or lower. Specifically it is a plasma stable at a plasma system pressure of 10 Torr or lower, generally from 0.1 mTorr to 10 Torr.

The plasma polymerized film obtained according to the process of the present invention, when employing the same organic compound as the monomer, is considerably smaller in coefficient of friction as compared with the plasma polymerized film obtained according to the continuous plasma polymerization method of the prior art, and it is also possible to make the coefficient of friction markedly smaller by appropriate selection of the organic compound which is the monomer.

Also, the above plasma polymerized film can be made excellent with respect to acid resistance, alkali resistance, solvent resistance, etc., by appropriate selection of the organic compound which is the monomer, and therefore, when these characteristics are required in combination with lubricity, or even when these characteristics are required without lubricity, it is useful as the surface protective film, etc.

Further, as the general characteristics of the plasma polymerized film obtained by the present invention, it has partially the structural features and the physical or chemical characteristics of the organic compound which is the monomer. For example, plasma polymerized film obtained when using an organic compound having amino group as the monomer will be a polymer having a large number of amino group and with excellent biocompatibility. Plasma polymerized film having biocompatibility in addition to the various characteristics described above is useful as a coating material for artificial organs, artificial blood vessels, artificial joints, artificial skin, and the like.

DETAILED DESCRIPTION OF THE INVENTION

Figure 1:
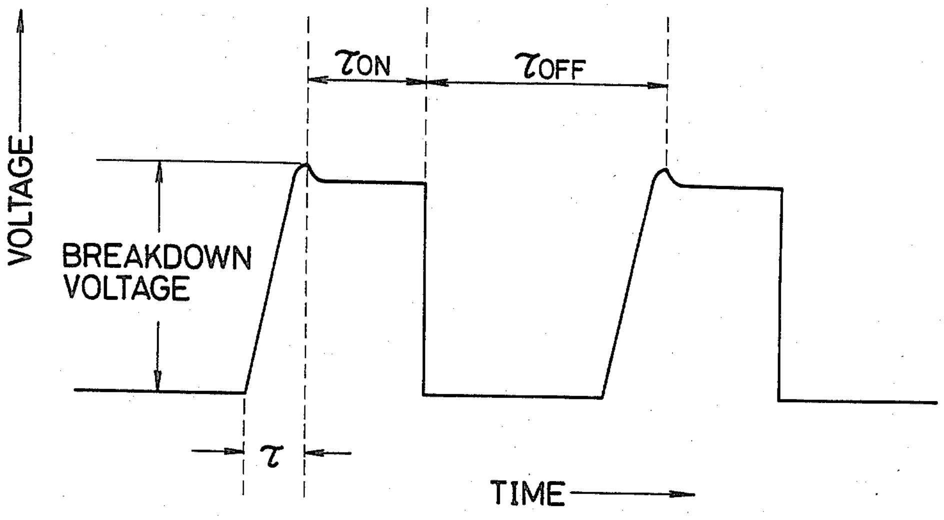
FIG. 1 is an illustration of an example of the wave form of the pulse discharging used in the present invention.

If pulse voltage is periodically applied to a gas, when the voltage for each pulse surpasses the gas breakdown voltage, gas breakdown will occur, initiating discharging, and discharging will stop when the applied voltage goes below a certain level. This is repeated periodically. In this specification, "pulse discharging" means discharging which is caused to occur periodically by the pulse voltage applied periodically to a gas. By "time of discharge condition in pulse discharging" is meant the time from the initiation of discharging by gas breakdown to the stopping of the discharging in one cycle of pulse discharging. By "time of non-discharge condition in pulse discharging" is meant the time from the stopping of the discharging to the subsequent initiation of discharging by gas breakdown in one cycle of pulse discharging. By "voltage rise time for gas breakdown" is meant the time from the time when the applied voltage is 0 V or one tenth as great as the voltage at the time of the discharge condition to the time when it surpasses the gas breakdown voltage. The voltage rise time for gas breakdown corresponds to the final portion of the time of non-discharge condition in the pulse discharging, and it is the time of transition from the non-discharge condition to the discharge conditions. Referring now to the illustration shown in FIG. 1, this figure shows an example of the wave form of the voltage when a direct current pulse voltage is applied to a gas to generate pulse discharging. In this figure, $\tau_{on}$ indicates the time of discharge condition in pulse discharging, $\tau_{off}$ indicates the time of non-discharge condition in pulse discharging, and $\tau$ indicates the voltage rise time for gas breakdown.

The time of the discharge condition, the time of the non-discharge condition and the voltage rise time for gas breakdown in a given pulse discharging can be measured by a commercially available wave form measuring instrument such as an oscilloscope, synchroscope, digital synchroscope, storage oscilloscope, digital storage oscilloscope and the like. The time of the discharge condition and the time of the non-discharge condition in pulse discharging can be controlled by connecting a commercially available function generator to a power amplifier and changing the form of the function. The voltage rise time for gas breakdown can be controlled by regulation of the voltage rise time and the set voltage in the pulse generator in the case of direct current discharge, while it can be controlled by selection of the frequency to be used and the control of the set voltage in the case of alternating current discharge and microwave discharge.

In the present invention, the voltage rise time for gas breakdown is an important factor. That is, as an electric field begins to be applied to the molecules of the organic compound which is the monomer, polarization of the organic compound molecules or acceleration of a trace of electrons and ions existing thermally will occur, and the polarization and acceleration are gradually enhanced until gas breakdown occurs to form a stable plasma state. The time from the application of the electric field until the formation of stable plasma state is the voltage rise time for gas breakdown, and the length of said time determines the properties of the plasma polymerized film formed.

In the process of the present invention, the voltage rise time for gas breakdown is required to be not longer than 100 msec., preferably 10 nsec. to 50 msec., more preferably 10 nsec. to 5 msec. If the voltage rise time for gas breakdown is longer than 100 msec., no effect of using pulse discharging can be obtained and the coefficient of friction of the plasma polymerized film obtained cannot be made small. Also, the time of the non-discharge condition in pulse discharging must be not shorter than 1 msec. If the time of the non-discharge condition is shorter than 1 msec., the plasma during previous discharging will frequently exist by after-glow at the time of the initiation of subsequent pulse discharging, whereby no effect of using pulse discharging can be obtained and it is not possible to lower the coefficient of friction of the plasma polymerized film obtained. The time of the discharge condition in pulse discharging may be generally 1 msec. to 10 sec., because the effect of using pulse discharging will become smaller if it is too long.

Other conditions ae not particularly limited. The discharging system employed may be any of, for example, direct current discharge, low frequency discharge, high frequency discharge and microwave discharge. Under typical conditions, the electron temperature of the plasma during discharging in the reaction zone of plasma polymerization, specifically, for example, in the region 1 to 3 cm apart in the vertical direction from the surface of the substrate, may be selected within the range of $0.5\times10^4$ to $8\times10^4$ K. Here, the electron temperature is measured according to the method by use of the probe for measurement of plasma characteristics as disclosed in U.S. Pat. No. 4,242,188, and it can be controlled to a desired value by changing the applied power for plasma excitation, discharging current, the gas pressure of the organic compound which is the monomer, the flow rate of said gas, the structure of electrodes and the position of the substrate to be treated. The flow rate of the gas containing the organic compound which is the monomer flowing into the plasma polymerization reactor may be, for example, 0.01 to 500 ml (STP)/min. per 100 liters of inner volume of the plasma polymerization reactor. The temperature of the substrate during plasma polymerization is not particularly limited but is generally 0° to 300° C.

The plasma polymerization reactor used for plasma polymerization is not also particularly limited and any of internal electrode system and electrodless system may be available, and there is also no limitation with respect to the shape of electrode coils, or cavity or antenna structure in the case of microwave discharging. Conventional devices used for plasma polymerization can be utilized.

The organic compound which may be used as the monomer in the process of the present invention is not particularly limited, provided that it is a gas under the above-mentioned pressure for generating low temperature plasma. The organic compounds include substituted or unsubstituted hydrocarbon compounds and organometallic compounds. Examples of hydrocarbon compounds are saturated or unsaturated aliphatic or alicyclic hydrocarbons and aromatic hydrocarbons, and these may have substituents such as halogen atoms, including fluorine, chlorine, bromine and iodine, hydroxyl group, amino group, carboxyl group, mercapto group, amido group, imido group and others, and they may also contain ether linkages.

More specifically, aliphatic hydrocarbons include, for example, alkanes such as methane, ethane, propane, butane, pentane, hexane and the like; alkenes such as ethene, propene, butene, pentene and the like; dienes such as butadiene, isoprene, pentadiene, hexadiene and the like; alkynes such as acetylene, vinylacetylene and the like. Alicyclic hydrocarbons include, for example, cyclopropane, cyclobutane, cyclopentane and the like. Aromatic hydrocarbons include, for example, benzene, styrene, toluene, xylene, pyridine, thiophene, pyrrole, aniline, phenylenediamine, toluidine, benzenesulfonic acid, ethylbenzene, acetophenone, chlorobenzene, methyl benzoate, phenyl acetate, phenol, cresol, furan and the like.

Organic compounds which are particularly preferred for obtaining plasma polymerized films with low coefficient of friction are alkanes and halogenated alkanes, and the voltage rise time for gas breakdown should preferably be 10 nsec. to 5 msec. Alkanes preferably have 1 to 10 carbon atoms, more preferably 3 to 8 carbon atoms, as exemplified by methane, ethane, propane, butane, pentane, hexane, heptane, octane, nonane, decane and isomers of these. Among them, particularly preferred are propane, n-butane, n-pentane, n-hexane, n-heptane and n-octane. Halogenated alkanes are those in which at least one hydrogen atom in alkanes is substituted by a halogen atom such as fluorine, chlorine, bromine or iodine, preferably fluorine atom or chlorine atom, having preferably 1 to 10 carbon atoms, more preferably 2 to 6 carbon atoms. Such halogenated alkanes include, for example, monofluoromethane, difluoromethane, trifluoromethane, tetrafluoromethane, monochloromethane, dichloromethane, trichloromethane, tetrachloromethane, monofluorodichloromethane, monofluoroethane, trifluoroethanes, tetrafluoroethanes, pentafluoroethane, hexafluoroethane, dichloroethanes, tetrachloroethanes, hexachloroethane, difluorodichloroethanes, trifluorotrichloroethanes, monofluoropropanes, trifluoropropanes, pentafluoropropanes, perfluoropropane, dichloropropanes, tetrachloropropanes, hexachloropropanes, perchloropropane, difluorodichloropropanes, tetrafluorodichloropropanes, bromomethane, methylene dibromide, bromoform, carbon tetrabromide, tetrabromoethanes, pentabromoethane, methyl iodide, diiodomethane, monofluorobutanes, trifluorobutanes, tetrafluorobutanes, octafluorobutanes, difluorobutanes, monofluoropentanes, pentafluoropentanes, octachloropentanes, perchloropentanes, trifluorotrichloropentanes, tetrafluorohexanes, nonachlorohexanes, pentafluorotrichlorohexanes, tetrafluoroheptanes, hexafluoroheptanes, trifluoropentachloroheptanes, difluorooctanes, pentafluorooctanes, difluorotetrafluorooctanes, monofluorononanes, hexafluorononanes, decachlorononanes, heptafluorohexachlorononanes, difluorodecanes, pentafluorodecanes, tetrachlorodecanes, tetrafluorotetrachlorodecanes, octadecachlorodecanes and the like. Particularly preferable halogenated alkanes are monofluoroethane, difluoroethanes, trifluoroethanes, tetrafluoroethanes, pentafluoroethane, monofluoropropanes, difluoropropanes, trifluoropropanes, tetrafluoropropanes, pentafluoropropanes, monofluoropropanes, difluorobutanes, trifluorobutanes, tetrafluorobutanes and pentafluorobutanes.

Also, preferred as organic compounds for obtaining plasma polymerized films with particularly low coefficient of friction are halogenated unsaturated hydrocarbons such as monofluoroethylene, difluoroethylenes, trifluoroethylene, tetrafluoroethylene, monochloroethylene, dichloroethylenes, trichloroethylene, tetrachloroethylene, monofluorobenzene, difluorobenzenes, tetrafluorobenzenes, hexafluorobenzene and the like. For these compounds, the voltage rise time for gas breakdown is preferably 10 nsec. to 5 msec.

According to the continuous plasma polymerization process of the prior art, it has been impossible to obtain a plasma polymerized film enriched in aromatic rings, because aromatic rings will be destroyed during the polymerization process even if an aromatic hydrocarbon such as styrene may be used as the organic compound which is the monomer. Also, it has been impossible to obtain a plasma polymerized film enriched in functional groups such as amino group or hydroxyl group, because these functional groups will also be destroyed in the polymerization process even if organic amines or alcohols having such functional groups may be used as the organic compound which is the monomer. In contrast, the process of the present invention is advantageous in that when an aromatic hydrocarbon is used as the monomer, there can be obtained a plasma polymerized film with low coefficient of friction and enriched in aromatic rings, while, when a compound having functional groups is used as the monomer, there can be obtained a plasma polymerized film with low coefficient of friction and enriched in the functional groups.

The plasma polymerized film enriched in aromatic rings has permselectivity for aromatic hydrocarbons and therefore, for example, it is useful as a separation membrane for separating styrene from a mixture of styrene and methanol. Preferable aromatic hydrocarbons for obtaining such a plasma polymerized film include, for example, benzene, styrene, phenol, toluene, xylene, chlorobenzene and the like. For these compounds, the voltage rise time for gas breakdown is preferably 1 μsec. to 4 msec.

The plasma polymerized film enriched in amino groups or mercapto groups has biocompatibility, and therefore it is suitable for surface coating of cell cultivation bed, artificial organs, artificial blood vessels, artificial bones, carriers for diagnostic reagents, biosensors, etc. Preferable organic amines for obtaining such a plasma polymerized film include, for example, ethylamine, methylamine, propylamine, ethylenediamine, allylamine, aniline, phenylenediamine, toluidine, hexamethylenediamine and the like. Examples of mercaptans are methylmercaptan, ethylmercaptan and the like. For these compounds, the voltage rise time for gas breakdown is preferably 1 μsec. to 25 μsec. According to the continuous plasma polymerization of the prior art, when employing a compound with low molecular weight such as ethylamine, methylmercaptan, etc., as the monomer, it has been particularly difficult to permit amino group or mercapto group to remain in the plasma polymerized film. However, the process of the present invention is advantageous in giving a film enriched in these functional groups by use of these monomers, because use of these organic compounds with low molecular weights as the monomer can give the advantages such that the amount of the monomer flowing into the plasma polymerization reactor can be controlled with ease due to the greater vapor pressure thereof and also that a uniform film with large area can be obtained due to rapid gas diffusion velocity.

The plasma polymerized film enriched in hydroxyl group or carboxyl group is highly hydrophilic and therefore it is useful for surface coating of articles for which wettability with water is demanded, such as contact lens. Also, it is useful for improvement of coating, dyeing and adhesion characteristics by modification of the surface of plastic moldings. Preferable organic compounds for obtaining such a plasma polymerized film are compounds having hydroxyl groups or carboxyl groups, as exemplified by alcohols such as methanol, ethanol, ethylene glycol, isopropanol, butanol and the like; hydroxybenzenes and hydroxyalkylbenzenes such as phenol, pyrocatechin, resorcin, hydroquinone, pyrogallol, cresol and the like; carboxylic acids such as formic acid, acetic acid, propionic acid, acrylic acid, oxalic acid, malonic acid, succinic acid, glycolic acid, lactic acid and the like. For these compounds, the voltage rise time for gas breakdown is preferably 10 nsec. to 1 μsec.

Organometallic compounds which may be used in the process of the present invention include, for example, those containing tin, silicon, germanium, aluminum, magnesium, calcium, zinc, cadmium, beryllium, lead, etc., as the metal element. Typical examples of the compounds include organic tin compounds such as tetramethyltin and the like; organic silicon compounds such as tetramethylsilane, trimethylsilane and the like. When these organometallic compounds are used as the monomer, the voltage rise time for gas breakdown is preferably 1 nsec. to 1 μsec., whereby there is the advantage that a plasma polymerized film which has smooth surface like a metal having a low coefficient of friction and a metallic luster can be obtained.

The above organic compounds may be used either singly or in combination of two or more compounds. When employing a combination of two or more organic compound gases, a gas mixture of the respective gases may be introduced into the plasma polymerizer, or alternatively they can be introduced separately into the plasma polymerizer and mixed in the polymerizer. Also, the gases containing these organic compounds provided for plasma polymerization may be mixed with a carrier gas of an inert gas such as argon, helium, xenon, neon and the like before introduction into the plasma polymerization reactor. Further, to the gases may be added, as required, gases such as nitrogen, hydrogen, oxygen, carbon monoxide, carbon dioxide, nitrogen monoxide, nitrogen dioxide, sulfur hexafluoride, fluorine.

In the process of the present invention, the plasma polymerized film is formed on the surface of a substrate placed in the reaction zone of plasma polymerization. The substrate may include, in addition to the examples as already mentioned, magnetic recording media such as magnetic tapes, magnetic discs and the like. Particularly, a thin metal film type magnetic recording medium in which the magnetic recording layer formed on a non-magnetic support comprises a thin metal film (e.g. thin cobalt (film) has a large coefficient of friction due to the thin metal film. Therefore, it is markedly effective to employ the plasma polymerized film according to the present invention. Also, Japanese Laid-open Patent Publication No. 179632/1984 discloses a process for forming a protective film on the surface of a magnetic recording medium according to plasma polymerization. It is also possible to enhance lubricity by forming further plasma polymerized film according to the process of the present invention on such a protective film thereby further enhancing the durability of such magnetic recording media. Examples of the substrate include structural elements such as gears, shafts, bearings, cams, pistons, cylinders, chains, wires, etc. made of metals, plastics or ceramics; members such as heads, guide poles, reels for videos or tape recorders; outer surfaces of ship or boats and various screws; inner surfaces of hoses; inner surfaces of various pumps; inner nozzle surfaces of extruders; surfaces of O-rings for shielding of movable portions; surfaces of skiing plates, artificial joints and other articles. Thus, coefficient of friction of the sliding surfaces of these substrates can be made smaller by the plasma polymerized film formed thereon.

According to the process of the present invention, a plasma polymerized film can be formed uniformly with a thickness of 3 Å to 1 μm on the surface of a substrate disposed in the reaction zone by plasma polymerization for about 1 minute to 1 hour. The plasma polymerized film has practical durability even when it is a very thin film with an average thickness of about 3 to 50 Å.

The process of the present invention is now described in more detail by referring to the following examples, to which the present invention is not limited.

EXAMPLES

Examples 1-11, Comparative Examples 1-18

Figure 2:
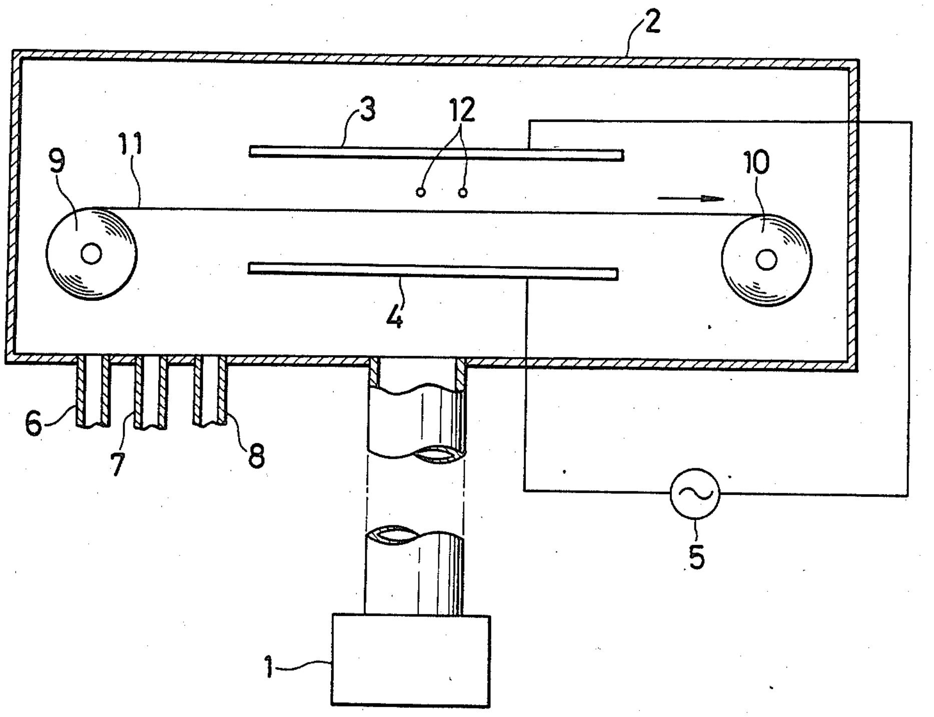
FIG. 2 is a longitudinal sectional view representing schematically the device for forming a plasma polymerized film on the substrate tape surface of a magnetic recording medium.

By means of the device shown in FIG. 2, a plasma polymerized film was formed on the surface of the substrate tape for magnetic recording media. The device shown in FIG. 2 has a pair of electrodes 3 and 4 opposed to each other in a plasma polymerization reactor 2 connected to a vacuum pump 1 and these electrodes are connected to an alternate current power source (20 KHz) 5. The alternate power source is equipped with a function generator and an amplifier, and pulsing is possible by the burst control of the function generator. The voltage rise time for gas breakdown in pulse discharging is controlled to 12.5 μsec. Pipes 6, 7 and 8 for feeding gaseous organic compounds are connected to the plasma polymerization reactor 2 at the bottom thereof. These feeding pipes for organic compounds are equipped with flow rate controlling valves (not shown). At the side wall of the plasma polymerization reactor 2, there is provided a pressure gauge (not shown) for monitoring the gas pressure within the polymerization reactor. The substrate tape 11 for magnetic recording media to be treated wound up on a first roll 9 runs continuously between the two electrodes 3 and 4 during operation and is wound up on a second roll 10. In the region between the electrodes 3 and 4, the aforementioned probe 12 disclosed in U.S. Pat. No. 4,242,188 is disposed at the position 2 cm apart from the tape to be treated.

In the operation of this device, one or more monomer compounds are fed under gaseous state while evacuating the inside of the plasma polymerization reactor 2 by means of a vacuum pump. When plasma is excited by discharging between the electrodes 3 and 4, a plasma polymerized film is formed on the surface of the substrate tape 11 running between the electrodes. The electron temperature of the plasma in the reaction zone is measured by the probe 12, and it is controlled to a desired value by changing the discharging current, the gas pressure in the plasma polymerization reactor, the flow rates of the monomer compounds and so on.

In these Examples and Comparative Examples, a long polyethyleneterephthalate film with a thickness of 12 μm and a width of 10 cm obliquely vapor deposited with a thin cobalt-nickel magnetic film (nickel content; 20 weight %) with a thickness of 100 nm on the surface thereof was used as the substrate tape for magnetic recording media and a plasma polymerized film was formed by means of the device shown in FIG. 2 on the thin cobalt-nickel magnetic layer to obtain a magnetic recording medium. In Examples 1 and 2 and Comparative Examples 1 and 2, a single layer plasma polymerized film was formed on the substrate tape, while in Examples 3, 4 and 5 and Comparative Examples 3 and 4, after formation of a first layer of plasma polymerized film, a second layer of plasma polymerized film of a different kind was formed as the overlayer thereon.

The plasma polymerization conditions in respective Examples and Comparative Examples, namely the kinds and flow rates of organic compounds, discharging system, discharging current (in the case of pulse discharging, current during the time of discharge condition), running speed of the substrate tape and the thickness of the plasma polymerized film formed are shown in Table 1 and Table 2. Table 1 concerns the case of forming a single layer of plasma polymerized film and the first layer (lower layer) in the case of forming two layers, and Table 2 concerns the second layer (upper layer) in the case of forming two layers. In Table 1 and Table 2, the thickness of the plasma polymerized film was evaluated by measuring the plasma polymerized film formed on the surface of a silicon wafer run simultaneously with the substrate tape by means of an ellipsometer and regarding the measured value as the thickness of the plasma polymerized film formed on the substrate tape.

The coefficient of dynamic friction ($\mu$) of the surface of the magnetic recording medium tape having the plasma polymerized film formed on its surface as described above was measured by the method shown in FIG. 3. In this method, a tape 22 mounted with a weight 21 of 50 g at one end was hanged at the upper half of a fixed stainless steel rod (SUS 420 J) 23 of 50 mm in diameter, led downward vertically and thereafter, through a freely rotatable roll 24, in the horizontal direction and connected at the other end to a tension detector 25. The tension detector 25 is equipped with a mechanism capable of tensioning and relaxing the tape and reciprocates the tape 22 with a stroke of 5 cm at a speed of 20 mm/sec. During going (when the tape 22 is drawn toward the tension detector), the tension $T_2$ is measured and the coefficient of dynamic friction is determined according to the following formula $T_2/T_1 = \exp(\mu\pi)$ wherein $T_1 = 50$ g (load by the weight 21).

Figure 3:
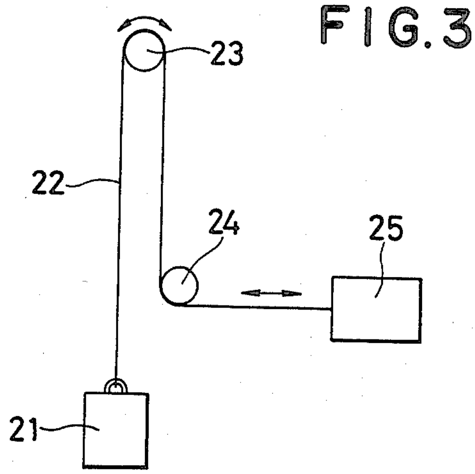
FIG. 3 is an illustration for explanation of the method for measuring the coefficient of dynamic friction of the tape surface of a magnetic recording medium.

According to the above method, the initial value of the coefficient of dynamic friction in the contact between the magnetic recording medium tape surface having the plasma polymerized film formed thereon and the stainless steel rod and the coefficient of dynamic friction after reciprocating the tape 22 1000 times by means of the device shown in FIG. 3 were measured. Also, by observation of the tape surface after 1000 times reciprocation with naked eyes and by an optical microscope (×100), the state in which abraded matters were sticked on the stainless steel rod 23 was examined. The results of these measurements are shown in Table 3.

TABLE 1

Formation of single layer or first layer plasma polymerized film*1

| | Organic compound (molar ratio) | Gas flow rate (ml(STP)/min.) | Discharging*2 conditions (Non-discharge time-discharge time, sec.) | Discharging current under discharge condition (mA) | Running speed of substrate tape (m/min.) | Thickness of plasma polymerized film (Å) |
|---|---|---|---|---|---|---|
| Example 1 | $CH_3CH_2CH_2CH_3$ | 30 | Pulse (1-1) | 50 | 0.25 | 80 |
| Example 2 | $CH_3CH_2CH_2CH_3$ | 30 | Pulse (5-1) | 50 | 0.20 | 90 |
| Example 3 | $CH_4 + CF_4$ (1:1) | 20 | Continuous | 120 | 0.15 | 80 |
| Example 4 | $CH_4 + CF_4$ (1:1) | 20 | " | 120 | 0.15 | 80 |
| Example 5 | $CH_3CH_2CH_2CH_3$ | 30 | " | 100 | 0.2 | 20 |
| Example 6 | $CH_2CH_2$ | 30 | Pulse (0.5-0.5) | 100 | 0.20 | 100 |
| Example 7 | $CH_2CHCHCH_2$ | 30 | " | 90 | 0.10 | 90 |
| Example 8 | $C_6H_{12}$ | 30 | " | 70 | 0.15 | 90 |
| Example 9 | $C_6H_6$ | 30 | " | 80 | 0.10 | 80 |
| Example 10 | $CF_2CF_2$ | 30 | " | 80 | 0.10 | 90 |
| Example 11 | $CH_2CHCOOH$ | 30 | " | 80 | 0.15 | 80 |
| Comparative Example 1 | $CH_3CH_2CH_2CH_3$ | 30 | Continuous | 70 | 0.3 | 100 |
| Comparative Example 2 | $CH_2{=}CH{-}CH{=}CH_2$ | 30 | " | 60 | 0.3 | 100 |
| Comparative Example 3 | $CH_4 + CF_4$ (1:1) | 20 | " | 120 | 0.15 | 80 |
| Comparative Example 4 | $CH_2{=}CH{-}CH{=}CH_2$ | 25 | " | 70 | 0.3 | 90 |
| Comparative Example 5 | $C_4H_{10}$ | 30 | Pulse (0.0005-0.0005) | 150 | 0.25 | 100 |
| Comparative Example 6 | $CH_4 + CF_4$ (1:1) | 30 | " | 120 | 0.20 | 120 |
| Comparative Example 7 | $CH_2CHCHCH_2$ | 30 | " | 90 | 0.10 | 100 |
| Comparative Example 8 | $C_6H_{12}$ | 30 | " | 70 | 0.15 | 110 |
| Comparative Example 9 | $C_6H_6$ | 30 | " | 80 | 0.10 | 110 |
| Comparative Example 10 | $CF_2CF_2$ | 30 | " | 80 | 0.10 | 120 |
| Comparative Example 11 | $CH_2CHCOOH$ | 30 | Pulse | 80 | 0.15 | 90 |
| Comparative Example 12 | $C_4H_{10}$ | 30 | Continuous | 150 | 0.25 | 120 |
| Comparative Example 13 | $CH_4 + CF_4$ (1:1) | 30 | " | 120 | 0.20 | 120 |
| Comparative Example 14 | $CH_2CHCHCH_2$ | 30 | " | 90 | 0.10 | 100 |
| Comparative Example 15 | $C_6H_{12}$ | 30 | " | 70 | 0.15 | 110 |
| Comparative Example 16 | $C_6H_6$ | 30 | " | 80 | 0.10 | 110 |
| Comparative Example 17 | $CF_2CF_2$ | 30 | " | 80 | 0.10 | 120 |
| Comparative | $CH_2CHCOOH$ | 30 | " | 80 | 0.15 | 90 |

TABLE 1-continued

| | Formation of single layer or first layer plasma polymerized film*1 | | | | | |
|---|---|---|---|---|---|---|
| | Organic compound (molar ratio) | Gas flow rate (ml(STP)/min.) | Discharging*2 conditions (Non-discharge time-discharge time, sec.) | Discharging current under discharge condition (mA) | Running speed of substrate tape (m/min.) | Thickness of plasma polymerized film (Å) |
| Example 18 | | | | | | |

Remarks:
*1Inner pressure in the plasma polymerization reactor during plasma polymerization are all 50 mTorr. The electron temperature of plasma (provided during the time of discharge condition in the case of pulse discharging) is controlled to within $0.5 \times 10^4$ to $8 \times 10^4$ K.
*2The voltage rise time for gas breakdown is 12.5 sec. Non-discharge time means the time for non-discharge condition in pulse discharging. Discharge time means the time for discharge condition in pulse discharging.

TABLE 2

| | Formation of second layer plasma polymerized film*1 | | | | | | |
|---|---|---|---|---|---|---|---|
| | Organic compound (molar ratio) | Gas flow rate (ml(STP)/-min.) | Discharging*2 conditions (Non-discharge time-discharge time, sec.) | Discharging current under discharge condition (mA) | Running speed of substrate tape (m/min.) | Thickness of plasma polymerized film (2nd layer) (Å) | Whole thickness of plasma polymerized films (Å) |
| Example 1 | — | | | | | 0 | 80 |
| Example 2 | — | | | | | 0 | 90 |
| Example 3 | $CH_3CH_2CH_2CH_3$ | 30 | Pulse (1-1) | 50 | 0.5 | 40 | 120 |
| Example 4 | $CH_3CH_2CH_2CH_3$ | 30 | Pulse (5-1) | 50 | 0.4 | 45 | 125 |
| Example 5 | $CH_3CH_2CH_2CH_3$ | 30 | " | 60 | 0.7 | 30 | 100 |
| Example 6 | — | | | | | 0 | 100 |
| Example 7 | — | | | | | 0 | 90 |
| Example 8 | — | | | | | 0 | 90 |
| Example 9 | — | | | | | 0 | 80 |
| Example 10 | — | | | | | 0 | 90 |
| Example 11 | — | | | | | 0 | 80 |
| Comparative Example 1 | — | | | | | 0 | 100 |
| Comparative Example 2 | — | | | | | 0 | 100 |
| Comparative Example 3 | $CH_3CH_2CH_2CH_3$ | 30 | Continuous | 70 | 0.9 | 30 | 110 |
| Comparative Example 4 | $CH_2{=}CHCH{=}CH_2$ | 25 | " | 70 | 1.0 | 20 | 110 |
| Comparative Example 5 | — | | | | | 0 | 100 |
| Comparative Example 6 | — | | | | | 0 | 120 |
| Comparative Example 7 | — | | | | | 0 | 100 |
| Comparative Example 8 | — | | | | | 0 | 110 |
| Comparative Example 9 | — | | | | | 0 | 110 |
| Comparative Example 10 | — | | | | | 0 | 120 |
| Comparative Example 11 | — | | | | | 0 | 90 |
| Comparative Example 12 | — | | | | | 0 | 120 |
| Comparative Example 13 | — | | | | | 0 | 120 |
| Comparative Example 14 | — | | | | | 0 | 100 |
| Comparative Example 15 | — | | | | | 0 | 110 |
| Comparative Example 16 | — | | | | | 0 | 110 |
| Comparative Example 17 | — | | | | | 0 | 120 |
| Comparative Example 18 | — | | | | | 0 | 90 |

Remarks:
*1Inner pressure in the plasma polymerization reactor during plasma polymerization are all 50 mTorr. The electron temperature of plasma (provided during the time of discharge condition in the case of pulse discharging) is controlled to within $0.5 \times 10^4$ to $8 \times 10^4$ K
*2The voltage rise time for gas breakdown is 12.5 sec.

TABLE 3

| | Initial value of coefficient of dynamic friction (μ) | Coefficient of dynamic friction after 1000 times reciprocal friction (μ) | Result of*1 observation of abrasion after 1000 times reciprocal friction |
|---|---|---|---|
| Example 1 | 0.23 | 0.25 | A |
| Example 2 | 0.22 | 0.25 | A |
| Example 3 | 0.23 | 0.24 | A |
| Example 4 | 0.23 | 0.25 | A |
| Example 5 | 0.22 | 0.26 | A |
| Example 6 | 0.28 | 0.30 | A |
| Example 7 | 0.29 | 0.31 | A |
| Example 8 | 0.24 | 0.26 | A |
| Example 9 | 0.28 | 0.30 | A |
| Example 10 | 0.19 | 0.21 | A |
| Example 11 | 0.22 | 0.24 | A |
| Comparative Example 1 | 0.43 | >0.7 | B |
| Comparative Example 2 | 0.45 | >0.7 | B |
| Comparative Example 3 | 0.51 | >0.7 | B |
| Comparative Example 4 | 0.42 | >0.7 | B |
| Comparative Example 5 | 0.38 | 0.47 | B |
| Comparative Example 6 | 0.42 | 0.60 | B |
| Comparative Example 7 | 0.44 | 0.55 | B |
| Comparative Example 8 | 0.39 | 0.44 | B |
| Comparative Example 9 | 0.38 | 0.57 | B |
| Comparative Example 10 | 0.32 | 0.45 | B |
| Comparative Example 11 | 0.34 | 0.40 | B |
| Comparative Example 12 | 0.39 | >0.7 | B |
| Comparative Example 13 | 0.44 | >0.7 | B |
| Comparative Example 14 | 0.45 | >0.7 | B |
| Comparative Example 15 | 0.40 | >0.7 | B |
| Comparative Example 16 | 0.40 | >0.7 | B |
| Comparative Example 17 | 0.35 | >0.7 | B |
| Comparative Example 18 | 0.37 | >0.7 | B |

Remarks:
*1A: No abraded matter recognized by optical microscope.
B: Adherent of white powdery abraded matter recognized with naked eyes.

EXAMPLE 12

Figure 4:
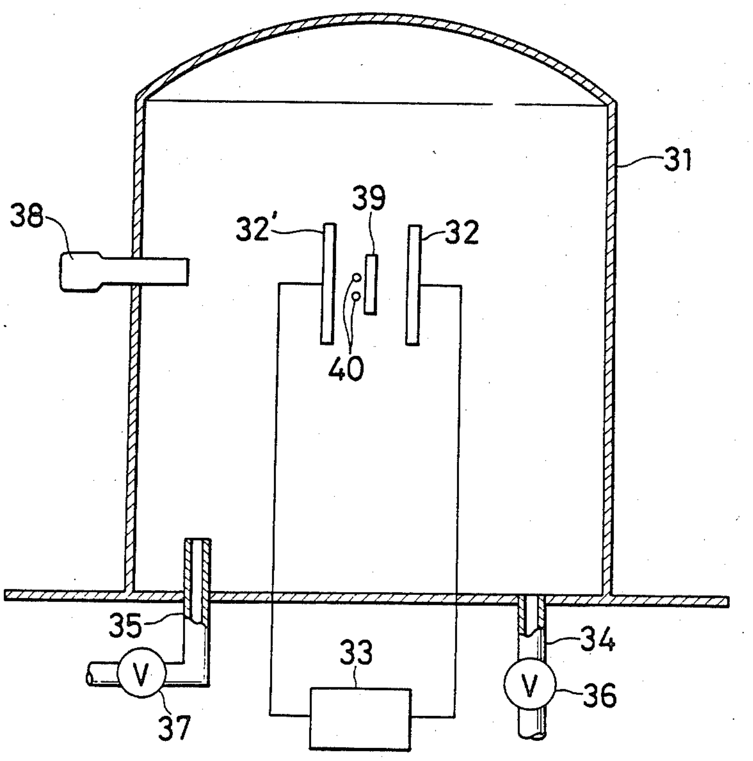
FIG. 4 is a longitudinal sectional view representing schematically another plasma polymerization reactor.

By means of the Bell-jar type plasma polymerization reactor shown in FIG. 4, plasma polymerized film from propane was formed by plasma polymerization by pulse discharging on the surface of a disc made of copper with a diameter of 50 mm and a thickness of 5 mm.

The plasma polymerization reactor 31 shown in FIG. 4 has parallel flat plate type electrodes 32 and 32', and these electrodes are connected to the power source 33 outside of the polymerization reactor. A pipe 35 for feeding a gaseous monomer compound is connected to the plasma polymerization reactor 31 at its bottom, and this pipe 35 is provided with a gas flow rate controlling valve 37. A vacuum pump (not shown) is connected through an evacuating pipe 34 to the plasma polymerization reactor at another site of the bottom, and the pipe 34 is provided with a valve 36 for controlling gas evacuating level. The plasma polymerization reactor 31 is equipped at its side wall with a pressure gauge for monitoring the pressure in the vessel.

The above copper disc is disposed as the substrate 39 between the electrodes 32 and 32', and the probe 40 disclosed in U.S. Pat. No. 4,242,188 is disposed at a position 2 cm apart from the substrate 39 for measuring the electron temperature of plasma.

In this Example, plasma polymerization was carried out by application of an alternate current of 20 KHz for 3 minutes under the conditions of a flow rate of propane of 10 ml (STP)/min., a pressure in the plasma polymerization reactor of 50 mTorr, pulse conditions: 0.8 sec. of the time of the discharge condition in pulse discharging, 0.2 sec. of the time of non-discharge condition, 12.5 μsec. of the voltage rise time for gas breakdown and 100 mA of discharging current during discharging. During this operation, the electron temperature of the plasma during the time of discharging was found to be $0.5\times10^4$ to $8\times10^4$ K. As a result, a plasma polymerized film with a thickness of 200 Å was formed on the surface of the copper disc. The film thickness was estimated by measuring the thickness of the plasma polymerized film formed on the surface of silicon wafer with a diameter of 50 mm and a thickness of 300 μm placed nearby the copper disc by an ellipsometer and regarding the measured thickness as that of the plasma polymerized film formed on the copper disc.

The coefficient of dynamic friction of the surface of the copper disc having the plasma polymerized film thus formed on its surface was measured as follows. That is, a hemisphere made of copper of 2 mm in diameter was mounted on one end of a rod, and the tip of the rod, namely said hemisphere, was urged under a load of 100 g weight vertically against the copper disc having the plasma polymerized film thereon at a distance of 20 mm from the center, and the coefficient of dynamic friction of the copper disc having the plasma polymerized film thereon was determined by measuring the force applied in the lateral direction on the rod while rotating the copper disc at 100 rpm. The coefficient of dynamic friction was measured at several temperatures of the copper disc and the copper hemisphere in contact therewith within the range of from 20° C. to 200° C., and the relationship between the coefficient of dynamic friction and temperature was examined. The results are shown in Table 4.

EXAMPLES 13–15

Plasma polymerized films were formed on the surface of copper discs in the same manner as in Example 12 except for changing the conditions of pulse discharging as shown in Table 4. The thicknesses of the plasma polymerized films formed in these Examples are also shown in Table 4. The coefficient of dynamic friction of the surfaces of the discs having thus formed plasma polymerized films on the surfaces were measured at various temperatures according to the same method as in Example 12. The results are shown in Table 4.

TABLE 4

| | Pulse discharging conditions: Time of discharge condition (sec.) | Time of non-discharge condition (sec.) | Plasma polymerization time (min.) | Thickness of plasma polymerized film (Å) | Coefficient of dynamic friction (μ): 20 (°C.) | 40 | 60 | 80 | 100 | 120 | 140 | 160 | 200 | 240 |
|---|---|---|---|---|---|---|---|---|---|---|---|---|---|---|
| Example 12 | 0.8 | 0.2 | 3 | 200 | 0.07 | 0.07 | 0.07 | 0.06 | 0.07 | 0.08 | 0.09 | 0.10 | 0.11 | 0.12 |
| Example 13 | 7 | 1 | 3 | 120 | 0.11 | 0.10 | 0.11 | 0.10 | 0.11 | 0.11 | 0.12 | 0.12 | 0.13 | 0.13 |
| Example 14 | 0.3 | 0.2 | 1.8 | 240 | 0.12 | 0.11 | 0.12 | 0.11 | 0.11 | 0.11 | 0.12 | 0.13 | 0.14 | 0.14 |
| Example 15 | 0.03 | 0.02 | 1.5 | 210 | 0.18 | 0.17 | 0.18 | 0.16 | 0.17 | 0.17 | 0.17 | 0.16 | 0.18 | 0.19 |

Note:
The voltage rise times for gas breakdown are all 12.5 μsec.

EXAMPLES 16-39 AND COMPARATIVE EXAMPLES 19 AND 20

Plasma polymerized films were formed on the surface of copper discs in the same manner as in Example 12 except that the conditions of pulse discharging were changed as shown in Table 5 and the gas pressure in the plasma polymerization reactor and polymerization time were changed to 500 mTorr and 1 hour, respectively. The thicknesses of the plasma polymerized films formed in the respective Examples and Comparative Examples are also shown in Table 5. The coefficient of dynamic friction of the surfaces of the copper discs having thus formed plasma polymerized films on the surfaces were measured at various temperatures according to the same method as in Example 12. The results are shown in Table 6.

TABLE 5

| | Organic compound | Power source | Voltage rise time for gas breakdown | Pulse discharging conditions (cycle-discharge time) (sec.) | Discharging current under discharge condition (mA) | Thickness of plasma polymerized film (Å) |
|---|---|---|---|---|---|---|
| Example 16 | $C_4H_{10}$ | DC | 10 nsec. | 1-0.5 | 100 | 5200 |
| Example 17 | " | " | 1 μsec. | " | " | 4800 |
| Example 18 | " | " | 100 μsec. | " | " | 5000 |
| Example 19 | " | " | 1 msec. | " | " | 5100 |
| Example 20 | " | " | 4 msec. | " | " | 4800 |
| Example 21 | " | " | 50 msec. | " | " | 4300 |
| Comparative Example 19 | " | " | 130 msec. | " | " | 4200 |
| Example 22 | " | AC | 250 nsec. (1 MHz) | " | 150 | 6300 |
| Example 23 | " | " | 2.5 μsec. (100 KHz) | " | 130 | 6000 |
| Example 24 | " | " | 12.5 μsec. (20 KHz) | " | 120 | 6100 |
| Example 25 | " | " | 250 nsec. (1 KHz) | " | 100 | 5800 |
| Example 26 | " | " | 2.5 msec. (100 Hz) | " | " | 5500 |
| Example 27 | " | " | 5 msec. (50 Hz) | " | " | 4800 |
| Example 28 | $C_2F_4$ | DC | 10 nsec. | " | 70 | 7000 |
| Example 29 | " | " | 1 μsec. | " | " | 6800 |
| Example 30 | " | " | 100 μsec. | " | 60 | 7000 |
| Example 31 | " | " | 1 msec. | " | " | 7200 |
| Example 32 | " | " | 4 msec. | " | " | 6800 |
| Example 33 | " | " | 50 msec. | " | " | 6500 |
| Comparative Example 20 | " | " | 130 msec. | " | " | 6300 |
| Example 34 | " | AC | 250 nsec. (1 MHz) | " | 100 | 8100 |
| Example 35 | " | " | 2.5 μsec. (100 KHz) | " | 90 | 7700 |
| Example 36 | $C_2H_4$ | " | 12.5 μsec. (20 KHz) | " | 85 | 7800 |
| Example 37 | " | " | 250 μsec. (1 KHz) | " | 80 | 7500 |
| Example 38 | " | " | 2.5 msec. (100 Hz) | " | 70 | 7000 |
| Example 39 | " | " | 5 msec. (50 Hz) | " | " | 7100 |

TABLE 6

| | Coefficient of dynamic friction (μ): 20° C. | 100° C. | 200° C. |
|---|---|---|---|
| Example 16 | 0.07 | 0.07 | 0.11 |
| Example 17 | 0.08 | 0.09 | 0.13 |
| Example 18 | 0.08 | 0.08 | 0.12 |
| Example 19 | 0.09 | 0.09 | 0.13 |

TABLE 6-continued

| | Coefficient of dynamic friction (μ): 20° C. | 100° C. | 200° C. |
|---|---|---|---|
| Example 20 | 0.10 | 0.11 | 0.13 |
| Example 21 | 0.37 | 0.37 | 0.39 |
| Comparative Example 19 | 0.44 | 0.45 | 0.48 |
| Example 22 | 0.07 | 0.07 | 0.10 |
| Example 23 | 0.08 | 0.09 | 0.11 |
| Example 24 | 0.07 | 0.09 | 0.10 |
| Example 25 | 0.09 | 0.10 | 0.12 |
| Example 26 | 0.10 | 0.12 | 0.14 |
| Example 27 | 0.11 | 0.13 | 0.15 |
| Example 28 | 0.06 | 0.06 | 0.06 |
| Example 29 | 0.05 | 0.06 | 0.06 |
| Example 30 | 0.06 | 0.06 | 0.07 |
| Example 31 | 0.07 | 0.06 | 0.07 |
| Example 32 | 0.07 | 0.07 | 0.08 |
| Example 33 | 0.25 | 0.29 | 0.33 |
| Comparative Example 20 | 0.30 | 0.37 | 0.45 |
| Example 34 | 0.06 | 0.06 | 0.07 |
| Example 35 | 0.07 | 0.07 | 0.07 |
| Example 36 | 0.07 | 0.08 | 0.08 |
| Example 37 | 0.07 | 0.08 | 0.09 |
| Example 38 | 0.08 | 0.08 | 0.10 |
| Example 39 | 0.09 | 0.09 | 0.14 |

EXAMPLES 40-45, COMPARATIVE EXAMPLES 21-23

Under the following conditions, according to the same procedure as in Example 12, plasma polymerized films were formed on the surfaces of copper discs (diameter 50 mm, thickness 5 mm) and silicon wafers (diameter 50 mm, thickness 300 μm).

Power source: DC power source,

Organic compound: ethylamine (flow rate 10 ml (STP)/min.),

Pressure: 100 mTorr,

Time of discharge condition in pulse discharging: 10 msec.,

Time of non-discharge condition in pulse discharging: 40 msec.,

Current during the time of discharge condition: 100 mA,

Polymerization time: 1 hr,

Electron temperature during the time of discharge condition: $3.7\times10^4$ to $4.0\times10^4$ K.

Under the same conditions as shown above except for changing the voltage rise time for gas breakdown to 2 msec., 4 msec., 6 msec., 8 msec., 10 msec. and 12 msec., plasma polymerized films were formed on the surfaces of copper discs and silicon wafers.

As Comparative Examples, under the same conditions as shown above except for effecting continuous discharging in place of pulse discharging at discharging current of 50 mA, 100 mA and 200 mA, plasma polymerized films were formed on the surfaces of copper discs and silicon wafers.

The thicknesses of the plasma polymerized films were determined by measuring those of the plasma polymerized film formed on the silicon wafers by means of an ellipsometer, and also the films were analyzed by Fourier Transform Infrared Spectroscopy (FT-IR) according to the transmission method. Prior to analysis, the FT-IR device was replaced internally with dry argon gas so that OH absorption exhibited by water may not appear in the IR spectrum. The area of the absorption band in the region of from 3300 to 3500 $cm^{-1}$ by amino group was measured. The relative values of the band areas in respective experiments were determined, taking the band area in the experiment in which continuous discharging was effected at a discharging current of 100 mA to be 1. The relative values obtained were estimated as representing relatively the contents of amino group. The results are shown in Table 7. The coefficient of dynamic friction of the surfaces of the copper discs having thus formed plasma polymerized films on their surfaces were measured at 20° C. according to the same method as in Example 12. The results are shown in Table 7.

TABLE 7

| | Discharging conditions | | | Plasma polymerized film | | |
|---|---|---|---|---|---|---|
| | Discharging system | Voltage rise time for gas breakdown (msec.) | Discharging current under discharge condition (mA) | Content of amino group | Thickness (Å) | Coefficient of dynamic friction (μ) |
| Example 40 | Pulse | 2 | 100 | 6.5 | 4700 | 0.29 |
| Example 41 | " | 4 | " | 3.0 | 4500 | 0.30 |
| Example 42 | " | 6 | " | 1.6 | 4600 | 0.34 |
| Example 43 | " | 8 | " | 1.1 | 4400 | 0.35 |
| Example 44 | " | 10 | " | 0.9 | 4200 | 0.37 |
| Example 45 | " | 12 | " | 1.0 | 4400 | 0.37 |
| Comparative Example 21 | Continuous | — | 50 | 0.8 | 5400 | 0.45 |
| Comparative Example 22 | " | — | 100 | 1.0 | 5800 | 0.47 |
| Comparative Example 23 | " | — | 200 | 0.9 | 6300 | 0.46 |

EXAMPLES 46-49, COMPARATIVE EXAMPLES 24-26

Under the following conditions, according to the same procedure as in Example 12, a plasma polymerized film was formed on the surface of a silicon wafer (diameter 50 mm, thickness 300 μm).

Power source: AC power source,

Organic compound: styrene (flow rate 10 ml (STP)/min.),

Pressure: 50 mTorr,

Time of discharge condition in pulse discharging: 10 msec.,

Time of non-discharge condition in pulse discharging: 40 msec.,

Current during the time of discharge condition: 100 mA,

Polymerization time: 1 hr,

Electron temperature during the time of discharge condition: $3.2\times10^4$ to $3.8\times10^4$ K.

Under the same conditions as shown above except for changing the voltage rise time for gas breakdown to 12.5 μsec., 16 μsec., 25 μsec. and 50 μsec., plasma polymerized films were formed on the surfaces of silicon wafers. Pulsing of applied power was effected by burst control of a low frequency generator (function generator), and the voltage rise time for gas breakdown was changed by changing the frequency of the power source to 5, 10, 15 and 20 KHz.

As Comparative Examples, under the same conditions as shown above except for effecting continuous discharging in place of pulse discharging at discharging current of 10 mA, 50 mA and 100 mA, plasma polymerized films were formed on the surfaces of silicon wafers.

The thicknesses of the plasma polymerized films were measured in the same manner as in Example 12, and also the films were analyzed by FT-IR according to the transmission method. The area of the absorption band in the region of 1450-1600 $cm^{-1}$ inherent in benzene ring was measured. The relative values of the band areas in respective experiments were determined, taking the band area in the experiment in which continuous discharging was effected at a discharging current of 100 mA to be 1, and the relative values obtained were estimated as representing relatively the contents of benzene rings. The results are shown in Table 8.

TABLE 8

| | Discharging conditions | | | Plasma polymerized film | |
|---|---|---|---|---|---|
| | Discharging system | Voltage rise time for gas breakdown (msec.) | Discharging current under discharge condition (mA) | Content of benzene ring | Thickness (Å) |
| Example 46 | Pulse | 12.5 (20 KHz) | 100 | 8.2 | 3600 |
| Example 47 | " | 16 (15 KHz) | " | 9.8 | 3400 |
| Example 48 | " | 25 (10 KHz) | " | 3.5 | 3500 |
| Example 49 | " | 50 (5 KHz) | " | 2.8 | 3800 |
| Comparative Example 24 | Continuous | — | 10 | 1.5 | 1200 |
| Comparative Example 25 | " | — | 50 | 1.2 | 3100 |
| Comparative Example 26 | " | — | 100 | 1.0 | 4200 |

EXAMPLES 50-61 AND COMPARATIVE EXAMPLES 27-30

Plasma polymerized films were formed in the same manner as in Examples 46-49 except that allylamine, ethylenediamine, propylamine or aniline was used in place of styrene and the voltage rise time for gas breakdown was changed to 2 msec., 4 msec. or 8 msec. As Comparative Examples, plasma polymerized films were formed using plasma by continuous discharging. The thicknesses of the plasma polymerized films thus obtained were determined in the same manner as in Example 12, and the films were analyzed by FT-IR according to the transmission method in the same manner as in Example 12. The results are shown in Table 9.

TABLE 9

| | | Discharging conditions | | Plasma polymerized film | | |
|---|---|---|---|---|---|---|
| | Organic compound | Discharging system | Voltage rise time for gas breakdown (msec.) | Content of amino group | Thickness (Å) | Coefficient of dynamic friction ($\mu$) |
| Example 50 | allylamine | Pulse | 2 | 6.2 | 5800 | 0.29 |
| Example 51 | " | " | 4 | 4.1 | 5600 | 0.28 |
| Example 52 | " | " | 8 | 1.3 | 5600 | 0.32 |
| Comparative Example 27 | " | Continuous | — | 1.0 | 6900 | 0.42 |
| Example 53 | Ethylenediamine | Pulse | 2 | 5.3 | 5500 | 0.30 |
| Example 54 | " | " | 4 | 4.8 | 5400 | 0.30 |
| Example 55 | " | " | 8 | 1.8 | 5800 | 0.35 |
| Comparative Example 28 | " | Continuous | — | 1.0 | 6800 | 0.47 |
| Example 56 | Propylamine | Pulse | 2 | 7.2 | 7100 | 0.26 |
| Example 57 | " | " | 4 | 6.8 | 6900 | 0.27 |
| Example 58 | " | " | 8 | 1.9 | 7500 | 0.33 |
| Comparative Example 29 | " | Continuous | — | 1.0 | 7900 | 0.45 |
| Example 59 | Aniline | Pulse | 2 | 6.9 | 6300 | 0.31 |
| Example 60 | " | " | 4 | 6.2 | 6200 | 0.30 |
| Example 61 | " | " | 8 | 1.4 | 6500 | 0.35 |
| Comparative Example 30 | " | Continuous | — | 1.0 | 7100 | 0.46 |

EXAMPLE 62 AND COMPARATIVE EXAMPLE 31

Under the following conditions, according to the same procedure as in Example 12, a plasma polymerized film was formed on the surface of a silicon wafer (diameter 50 mm, thickness 300 $\mu$m).

Power source: AC power source (13.56 MHz),
Organic compound: tetramethyltin (flow rate 10 ml (STP)/min.),
Pressure: 50 mTorr,
Time of discharge condition in pulse discharging: 10 msec.,
Time of non-discharge condition in pulse discharging: 40 msec.,
Voltage rise time for gas breakdown: 18 nsec.,
Current during the time of discharge condition: 100 mA,
Polymerization time: 1 hr,
Electron temperature during the time of discharge condition: $2.7\times10^4$ to $3.0\times10^4$ K.

As Comparative Examples, a plasma polymerized film was formed in the same manner as in the above example except for effecting continuous discharging in place of pulse discharging.

In the case of pulse discharging, a thin film with a thickness of 6500 Å like a metal having luster was obtained, and it was found to be a film with a smooth surface by observing by a scanning type electron microscope (×10000). On the other hand, in case of continuous discharging, particles with sizes of 5000 to 7000 Å were found to be dispersed on a thin film with a thickness of 1250 Å which is yellowish and transparent without luster.

We claim:

1. A process for producing a plasma polymerized film, which comprises:

forming a plasma polymerized film on the surface of a substrate placed in a reaction zone which is not in contact with an electrode by subjecting an organic compound containing gas to plasma polymerization utilizing low temperature plasma formed by pulse discharging, in which the time of the nondischarging condition is at least 1 msec. and the voltage rise time for gas breakdown is not longer than 100 msec.

2. The process according to claim 1, wherein the organic compound is at least one member selected from the group consisting of substituted or unsubstituted hydrocarbon compounds and organometallic compounds.

3. The process according to claim 1, wherein the organic compound is at least one member selected from the group consisting of alkanes and halogenated alkanes, and the voltage rise time for gas breakdown is 10 nsec. to 5 msec.

4. The process according to claim 1, wherein the organic compound is a halogenated unsaturated hydrocarbon and the voltage rise time for gas breakdown is 10 nsec. to 5 msec.

5. The process according to claim 1, wherein the organic compound is at least one member selected from the group consisting of aromatic hydrocarbon compounds and the voltage rise time for gas breakdown is 1 μsec. to 4 msec.

6. The process according to claim 1, wherein the organic compound is at least one member selected from the group consisting of organic amines and mercaptans and the voltage rise time for gas breakdown is 1 μsec. to 25 μsec.

7. The process according to claim 1, wherein the organic compound is an organometallic compound and the voltage rise time for gas breakdown is 1 nsec. to 1 μsec.

8. The process according to claim 1, wherein the voltage rise time for gas breakdown is 10 nsec. to 50 msec.

9. The process according to claim 1, the time of non-discharge condition in pulse discharging is 1 msec. to 10 sec.

10. The process according to claim 1, wherein the substrate is a magnetic recording medium substrate having a non-magnetic support and a magnetic recording layer provided thereon.

11. The process according to claim 1, wherein the plasma polymerized film has a thickness of 3 Å to 1 μm.

12. The process according to claim 11, wherein the thickness of said plasma polymerized film ranges from 3 to 50 Å.

13. The process according to claim 1, wherein the electron temperature of the plasma during discharging where the electrodes of the plasma polymerization vessel are about 1 to 3 cm apart in the vertical direction from the surface of the substrate is within the range of $0.5 \times 10^4$ to $8 \times 10^4$ K.

14. The process according to claim 1, wherein said organic compound is passed into the plasma polymerization reactor at a flow rate of 0.01 to 500 ml (STP)/min per 100 liters of volume of the plasma polymerization reactor.

* * * * *